(12) United States Patent
Nicolas et al.

(10) Patent No.: US 11,566,216 B2
(45) Date of Patent: Jan. 31, 2023

(54) CELL CULTURE INSERT AND DEVICE FOR CULTIVATING CELLS

(71) Applicant: BRAND GMBH + CO KG, Wertheim (DE)

(72) Inventors: Frank Nicolas, Wuerzburg (DE); Antonio Romaguera, Faulbach (DE); Peter Prokopp, Wertheim (DE)

(73) Assignee: BRAND GMBH + CO KG, Wertheim (DE)

( * ) Notice: Subject to any disclaimer, the term of this patent is extended or adjusted under 35 U.S.C. 154(b) by 882 days.

(21) Appl. No.: 16/325,426

(22) PCT Filed: Aug. 1, 2017

(86) PCT No.: PCT/EP2017/025225
§ 371 (c)(1),
(2) Date: Feb. 14, 2019

(87) PCT Pub. No.: WO2018/033253
PCT Pub. Date: Feb. 22, 2018

(65) Prior Publication Data
US 2019/0185801 A1 Jun. 20, 2019

(30) Foreign Application Priority Data
Aug. 18, 2016 (DE) .................... 20 2016 004 992.6
Sep. 20, 2016 (DE) .................... 20 2016 005 740.6

(51) Int. Cl.
*C12M 1/00* (2006.01)
*C12M 1/12* (2006.01)
(Continued)

(52) U.S. Cl.
CPC ............ *C12M 25/04* (2013.01); *C12M 23/12* (2013.01); *C12M 23/38* (2013.01); *C12M 23/46* (2013.01)

(58) Field of Classification Search
CPC ...... C12M 25/04; C12M 23/12; C12M 23/38; C12M 23/46
(Continued)

(56) References Cited

U.S. PATENT DOCUMENTS 5,358,871 A 10/1994 Stevens et al.
5,366,893 A 11/1994 Stevens et al.
(Continued)

FOREIGN PATENT DOCUMENTS

CN 201605273 U 10/2010
FR 2942239 A1 8/2010
(Continued)

*Primary Examiner* — Liban M Hassan
(74) *Attorney, Agent, or Firm* — David S. Safran; Calderon Safran & Cole P.C.

(57) ABSTRACT

A cell culture insert with a hollow cylindrical housing having an upper end-face opening delimited by an opening edge and a lower end-face base designed as a membrane, support feet being arranged on the base edge of the housing and/or on the base and at least one support arm. The legs protrude downward for supporting the housing on a support in a non-tipping manner with a small uniform spacing between the base and the support. The at least one support arm protrudes outwards at the opening edge and can be placed on an edge of a well plate in which a plurality of wells. The support arm is an edge hanging element, and for this purpose, has a support section that runs radially relative to the housing and a hanging section that runs from the support section downwards in the direction of the base of the housing.

4 Claims, 4 Drawing Sheets

(51) Int. Cl.
  *C12M 1/32* (2006.01)
  *C12M 3/00* (2006.01)
(58) Field of Classification Search
  USPC .......................................... 435/289.1, 297.5
  See application file for complete search history.

(56) References Cited

U.S. PATENT DOCUMENTS

| | | |
|---|---|---|
| 5,534,227 A | 7/1996 | Lahm et al. |
| 5,578,492 A | 11/1996 | Fedun |
| 7,598,076 B2 | 10/2009 | Wedell et al. |
| 8,058,060 B2 | 11/2011 | Esser et al. |
| 8,163,537 B2 | 4/2012 | Martin et al. |
| 8,501,462 B2 | 8/2013 | Eddington et al. |
| 9,139,804 B2 | 9/2015 | Dicke |
| 2006/0051857 A1 | 3/2006 | Wedell et al. |
| 2006/0172412 A1 | 8/2006 | Perrier et al. |
| 2008/0194017 A1 | 8/2008 | Esser et al. |
| 2010/0112690 A1 | 5/2010 | Eddington |
| 2010/0190197 A1* | 7/2010 | Martin .................. C12M 25/04 435/29 |
| 2012/0082600 A1 | 4/2012 | Esser et al. |
| 2012/0214226 A1 | 8/2012 | Dicke |
| 2013/0267019 A1* | 10/2013 | Schmidt ................ C12M 35/08 435/297.1 |
| 2015/0247112 A1* | 9/2015 | Orr ....................... C12M 23/12 506/9 |
| 2017/0226458 A1 | 8/2017 | Li et al. |

FOREIGN PATENT DOCUMENTS

| | | |
|---|---|---|
| WO | 9428111 A1 | 12/1994 |
| WO | 2010038013 A1 | 4/2010 |

* cited by examiner

CELL CULTURE INSERT AND DEVICE FOR CULTIVATING CELLS

BACKGROUND OF THE INVENTION

Field of the Invention

The invention relates to a cell culture insert having a hollow cylindrical housing with an upper end-face opening bordered by an upper edge of the housing and with a lower end-face bottom formed as a membrane. The cell culture insert has supporting feet being arranged on at least one of a bottom edge of the housing and the bottom of the housing. The supporting feet protrude downward for enabling the housing to be supported on a substrate in a tilt-proof manner with a small uniform distance between the bottom of the housing and the substrate. The cell culture insert further has a carrying arm, which protrudes outward from the housing on the upper edge of the housing for enabling the housing to be supported on an edge of a well of a well plate. The carrying arm is an edge suspension element having a supporting section running radially relative to the housing and a suspension section running downward from the supporting section in a direction toward the bottom of the housing. The invention also relates to a device for culturing cells comprising a well plate in which a plurality of wells is formed to hold liquid, wherein each well has a bottom and has a peripheral side wall protruding therefrom, wherein the side wall has a top edge terminating the side wall, and wherein each well has certain lateral inside dimensions in a plane parallel to the bottom, and wherein each well has a certain inside height in the direction perpendicular to the bottom. The device has a cell culture insert of a certain outside height, wherein the cell culture insert has a carrying arm for suspending of the culture insert on the top edge of the well and supporting feet. An outside height of the cell culture insert is less than the inside height of the well so that, with the cell culture insert being suspended, the supporting feet are located at a distance from the bottom of the well.

DESCRIPTION OF RELATED ART

Cell culture inserts of the type in question are generally used in so-called well plates. A well plate contains a plurality of so-called wells for holding liquid. These wells are normally molded in the well plate. Each well has a bottom, a peripheral side wall protruding therefrom and an edge terminating the side wall at the top. The edge borders the front side access opening into the well.

Liquid is added to the wells in the well plate. This is the culture medium for cells that are cultured on the bottom of the wells or on the bottom of a cell culture insert that is inserted into the well. The culture medium is added to the well and replaced by means of a pipette.

Cell culture inserts of the type in question are thus used to culture cells on the bottom of the cell culture inserts, wherein the bottom is embodied as a membrane. A plurality of carrying arms protruding laterally at the edge of the upper opening of the respective cell culture insert are generally used for suspending the cell culture inserts in the wells. Culturing the cells in the suspended insert at a relatively great distance from the bottom of the well makes it possible to add sufficient culture medium to the well and around the cell culture insert.

However, there are also culture methods in which the cell culture inserts stand on a substrate. For this purpose, the cell culture insert, on which the present invention is based (U.S. Pat. No. 5,578,492 A) has a total of six supporting feet protruding downward at the edge of the housing at the bottom, in addition to the total of four carrying arms protruding at the side at the edge of the upper opening. With these supporting feet, the housing of this cell culture insert can be deposited in a tilt-proof manner on a substrate with its bottom at a small uniform distance from the substrate.

The bottom of the cell culture insert is usually embodied as a microporous membrane. The membrane permits an exchange with the culture medium beneath the bottom of the insert when the cell culture insert is arranged in a well filled with culture medium in a well plate.

With the state of the art on which the invention is based (U.S. Pat. No. 5,578,492 A), the cell culture insert is formed of a thermoplastic polymer, for example, PE, PET, PP, which is provided with intended breaking lines on the house side of the carrying arms. The carrying arms can therefore be broken off the housing of the cell culture insert, so that the cell culture insert cannot become "stuck" on the peripheral edge of the well in the well plate, but instead can be deposited on its supporting feet in the desired location, for example, also in the well, so that the bottom of the cell culture insert still maintains a certain distance from the substrate, which is the bottom of the well in this case.

In the state of the art described previously, methods are described for how such a cell culture insert can be produced, in particular the material of which the bottom of the cell culture insert, which is designed as a membrane, is made and how this bottom can be mounted on the housing of the cell culture insert. Reference is made to this state of the art for this information from the state of the art. Such constructions of the cell culture insert can also be used within the scope of the teaching according to the present invention.

For introducing culture medium into the well or for removing culture medium from the well with the help of the pipette tip of a pipette, one needs a small amount of space at the side of the cell culture insert that has been inserted into the well. One thus needs at least one so-called feed-through window between the cell culture insert and the side wall of the well. This feed-through window is comparatively narrow with the cell culture insert provided in the state of the art, on which the present invention is based.

With other state-of-the-art constructions, the feed-through windows are comparatively narrow and therefore subject to problems (German Patent Application DE 10 2012 100 583 A1, and corresponding U.S. Pat. No. 9,139,804 B2). There have been attempts to solve this problem with an eccentric configuration of the cell culture insert in the well, again with a plurality of carrying arms (European Patent Application EP 1 532 237 B1, and corresponding U.S. Pat. No. 7,598,076 B2) distributed uniformly around the circumference. Other approaches have attempted to accomplish this with a special adaptation of the well plate and cell culture inserts, wherein asymmetrical recesses for making additions are provided in the well plate as the feed-through windows (U.S. Pat. No. 5,534,227 A; International Patent Application Publication WO 2006/131123 A2). Such constructions are complicated.

SUMMARY OF THE INVENTION

The present invention is based solving the problem of creating a cell culture insert that can be inserted either as a standing insert or as a suspended insert and easily ensures an adequate feed-through window in the well for either option. The object of the present invention is also to provide a corresponding device for culturing cells with a well plate and cell culture insert.

With a cell culture insert having the initially mentioned features, the solving of the problem described above is achieved through the features described herein.

According to the invention, the cell culture insert is provided with a specially designed carrying arm designed as an edge suspension element. Therefore, a single carrying arm protruding outward is sufficient to suspend the cell culture insert securely on the edge of a well. In this way, one no longer needs carrying arms that protrude outward, but instead basically only exactly one carrying arm to accomplish this.

With corresponding dimensions of the housing of the cell culture insert in comparison with the well of the well plate intended to receive it, there is thus a much greater distance from the side wall of the well on the side of the housing of the cell culture insert opposite the suspended carrying arm than on the side of the housing facing the carrying arm. One thus easily creates the desired feed-through window for the well on the side of the housing opposite the suspended carrying arm.

As already mentioned, it is basically sufficient to have a single carrying arm designed as an edge suspension element on the housing. Basically, however, it is also possible within the scope of the teaching of the invention to provide more than one carrying arm, designed as an edge suspension element, on the housing. For example, within the scope of the teaching of the invention, one might thus provide three carrying arms, each of which here is designed as an edge suspension element, distributed at approximately 120° intervals around the circumference of the edge of the opening of the housing.

However, the cell culture insert according to the invention is then expediently designed in this way if it has exactly one carrying arm designed as an edge suspension element.

It is important, in any case, that the outside height of the cell culture insert is less than the inside height of the well into which the cell culture insert is to be inserted, and thus, to achieve the result that, with the cell culture insert suspended in place, the supporting feet of the cell culture insert would be at a distance from the bottom of the well.

Depending on the lateral inside dimensions of the well, with which the cell culture insert according to the invention is to be used, the cell culture insert together with the carrying arm, although that is not to be used in this case, can be deposited on the bottom of the well of the well plate. This then yields a feed-through window for the well at the side of the carrying arm in the well, because the carrying arm on the edge of the opening of the cell culture insert protrudes outward and thus ensures a distance from the side wall of the well.

However, it may also be such that the lateral inside dimensions of the well with which the cell culture insert is to be used do not allow an insertion of the cell culture insert into the well with the carrying arm. In this case, one would have to break the carrying arm off the housing of the cell culture insert near the housing, as is known from the state of the art, in order to then be able to deposit the cell culture insert on the bottom of the well.

If a plurality of carrying arms are distributed on the edge of the circumference of the opening of the housing, then if one would like to deposit the cell culture insert on the bottom of the well, the lateral inside dimensions of the well must be larger than the lateral outside dimensions of the cell culture insert, taking into account the carrying arms. In this case, despite the presence of a plurality of carrying arms, one can only suspend a carrying arm on the well only if it is designed as an edge suspension element.

However, a special design of the well is needed if one wants to be able to simultaneously suspend the cell culture insert with all the carrying arms on the well at once when there is a plurality of carrying arms distributed on the edge of the circumference of the opening of the housing and nevertheless be able to deposit the cell culture insert on the bottom of the well. To do so, it is then necessary for the lateral geometric shape of the well to be asymmetrical relative to the lateral geometric shape of the housing of the cell culture insert. When there are three carrying arms, the well must be designed in the form of a triangle. In the arrangement of the carrying arms at the point of intersection of the inner circle of the well, the cell culture insert could be suspended on the edge of the well. In the arrangement of the carrying arms aligned with the circumference of the well, the cell culture insert could be deposited on the bottom of the well.

In any case, the invention achieves the result that cell cultures can be cultured with the cell culture insert in suspension and/or can be shipped in this way. With a suspended arrangement of the cell culture insert, a relatively great distance from the membrane of the cell culture insert to the bottom of the well can be predefined. Therefore, there is a relatively large volume in the well beneath the membrane of the cell culture insert. Therefore, more culture medium is available to cell cultures and tissue cultures that must be cultured at an air/liquid boundary layer. Such a cell culture insert, including the culture developed in it, can then be placed on the bottom of the well of a conventional well plate and transported, after being secured by a suitable embedding medium and protected by a cover.

According to a preferred embodiment of the invention, it is advisable for the inside clearance from the suspension section to the housing to be greater than the thickness of the edge of a well, thereby resulting in a clearance fit for the inserted cell culture insert in the well. Thus, the cell culture insert can easily be moved up and down in the well, i.e., suspended and then removed again.

Through the design of the carrying arm of the cell culture insert according to the invention, it is thus possible to predefine a determined position of the cell culture insert in the well. To do so, one may specify that the carrying arm of the cell culture insert according to the invention has an initial section which extends upward from the housing and to which the supporting section is connected, so that in the case of a housing oriented horizontally, the lower edge of the opening of the supporting section is higher than the edge of the opening.

The initial section may first run slightly up and outward from the edge of the opening, for example, and then develop into the supporting section. When suspended in the well, the edge of the opening of the cell culture insert is then in a plane significantly below the plane formed by the edge of the well.

The flexibility of the cell culture insert according to the invention is increased by the fact that the carrying arm has a predetermined breaking point by which the carrying arm can be broken off the housing. The predetermined breaking point is preferably designed as an arc of a circle. It is therefore less elastic. The cell culture insert can therefore be inserted by using the carrying arm, but later also without using the carrying arm. Thus, the cell culture insert according to the invention has a wide range of applications for different wells and different purposes.

It has repeatedly been difficult to handle a cell culture insert using a gripping tool, in particular tweezers, without making any mistakes. In particular, the cell culture insert must not be tilted or turned due to the gripping tool under the influence of the force being applied. According to the invention, the suspension section of the carrying arm here offers an excellent aid. The suspension section is designed like a web and can be gripped by tweezers. With a suitable design of the suspension section, for example, due to the fact that integral molded parts are provided on both sides of its upper edge, the tip of the tweezers can grip between these integral molded parts. The cell culture insert therefore cannot be turned or twisted in relation to the tip of the tweezers, but instead can be removed from the well or suspended in the well while in a stable position.

A construction of the cell culture insert according to the invention, in which exactly one carrying arm is provided on the housing, is most especially preferred. Thus, the cell culture insert hangs eccentrically in the well, and the region between the housing of the cell culture insert and the side wall of the well beyond the carrying arm is completely free. This results in a wide feed-through window for a pipette tip when the cell culture insert is suspended.

The housing of the cell culture insert suspended in the well with the carrying arm hangs at a slight inclination with respect to the well because of the play at the edge of the well. The position of the suspended cell culture insert can be stabilized by the fact that a three-point bearing of the housing on the side wall of the well is created by utilizing the suspension section of the carrying arm and the supporting feet. To achieve this, according to the preferred embodiment of the invention, it is provided that two supporting feet also protruding outward from the housing are arranged on the circumference on both sides of the housing and at the same distance from the carrying arm. By means of these two supporting feet on the side wall of the well, it is possible to achieve the result that a cell culture insert suspended in the well is arranged at an inclination of no more than 10° with respect to the well.

According to the preferred teaching of the invention, it is stipulated that exactly three supporting feet spaced equally on the circumference of the housing are provided so that the cell culture insert can sit securely without tilting when placed on a substrate.

If, according to the preferred embodiment, the supporting feet also protrude outward from the housing of the cell culture insert, this has the advantage that a gap is retained between the side wall of the well and the housing when the cell culture insert has been inserted into the well. This facilitates the replacement of culture medium. Furthermore, the membrane forming the bottom of the hollow cylindrical housing can be attached to the lower peripheral edge of the hollow cylindrical housing, so that the maximum area of the membrane can be utilized. If the distance toward the outside created by the supporting feet is of a sufficient dimension, a capillary effect can be prevented when the cell culture insert is immersed in culture medium, or at any rate it can be limited so that the liquid level in the well is essentially the same everywhere. Therefore, the membrane is always wetted with culture medium over the full area, and this prevents the development of areas of the membrane with little or no supply of culture medium.

A construction in which the housing of the cell culture insert is designed as a circular cylinder is most especially preferred, wherein the associated well of the well plate should then especially preferred also be designed as a circular cylinder accordingly.

From the technical standpoint of materials, it is advisable for the cell culture insert to be made of plastic, in particular a thermoplastic polymer. Reference may be made here again to the state of the art, which contains proposals for reasonable materials to use here.

The subject matter of the invention is also a device for culturing cells having the features described at the outset in which the problem defined above is solved.

The particular features of the configuration of a cell culture insert according to the invention in a well of a device for culturing cells were already presented above in conjunction with the explanation of the cell culture insert. Reference is herewith made to those explanations.

For the well plate, it is also true that it may be made of plastic, in particular a thermoplastic polymer. It is usually combined with an additional bottom plate or a bottom frame and often also has a cover. To this extent, reference may also be made to the state of the art cited in the introduction.

The invention will now be explained in greater detail on the basis of drawings illustrating just one preferred embodiment.

DETAILED DESCRIPTION OF THE INVENTION

The figures show a particularly preferred embodiment of a device for culturing cells that has a well plate 2 made of a thermoplastic polymer and is provided with a step 1 here. The well plate 2 contains a plurality of wells 3, namely a total of six wells here, for holding liquid. The well plate 2 has a top side 4, which extends over part of the area and on which the identifying numbers are provided in FIG. 1 and are integrally molded into the wells 3. The top side 4 is recessed in the spaces between the wells 3, so that the side walls 5 of the wells 3 can be seen there, because they are freely accessible.

Figure 1:
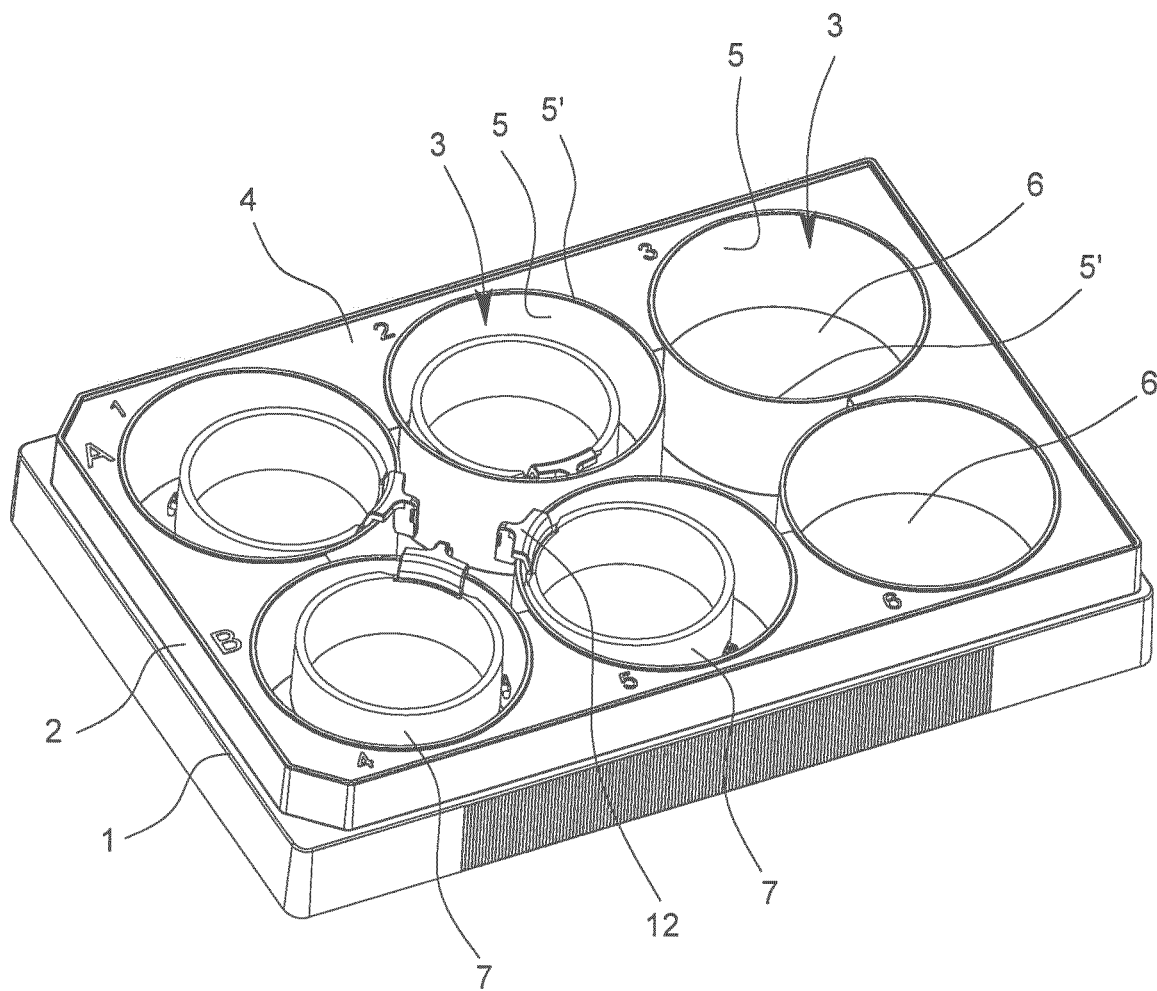
FIG. 1 is a perspective diagram of a device according to the invention for culturing cells with a well plate having a plurality of wells, namely here a total of six wells, to hold liquid, and having a plurality of cell culture inserts, namely here a total of four.

It can already be seen in FIG. 1 that each well 3 has a bottom 6 and the peripheral side wall 5 protruding therefrom, wherein the side wall 5 has an edge 5' terminating the side wall at the top. At the right of FIG. 1, it can be seen from the two empty wells 3 that each well 3 has lateral inside dimensions in a plane parallel to the bottom 6 and has a certain inside height in a direction perpendicular to the bottom 6. In the embodiment shown here, the wells 3 are designed to be cylindrical, so that the lateral inside dimensions are defined conclusively by a certain inside diameter. In the case of non-circular wells 3, there are more complicated lateral inside dimensions.

Figure 2:
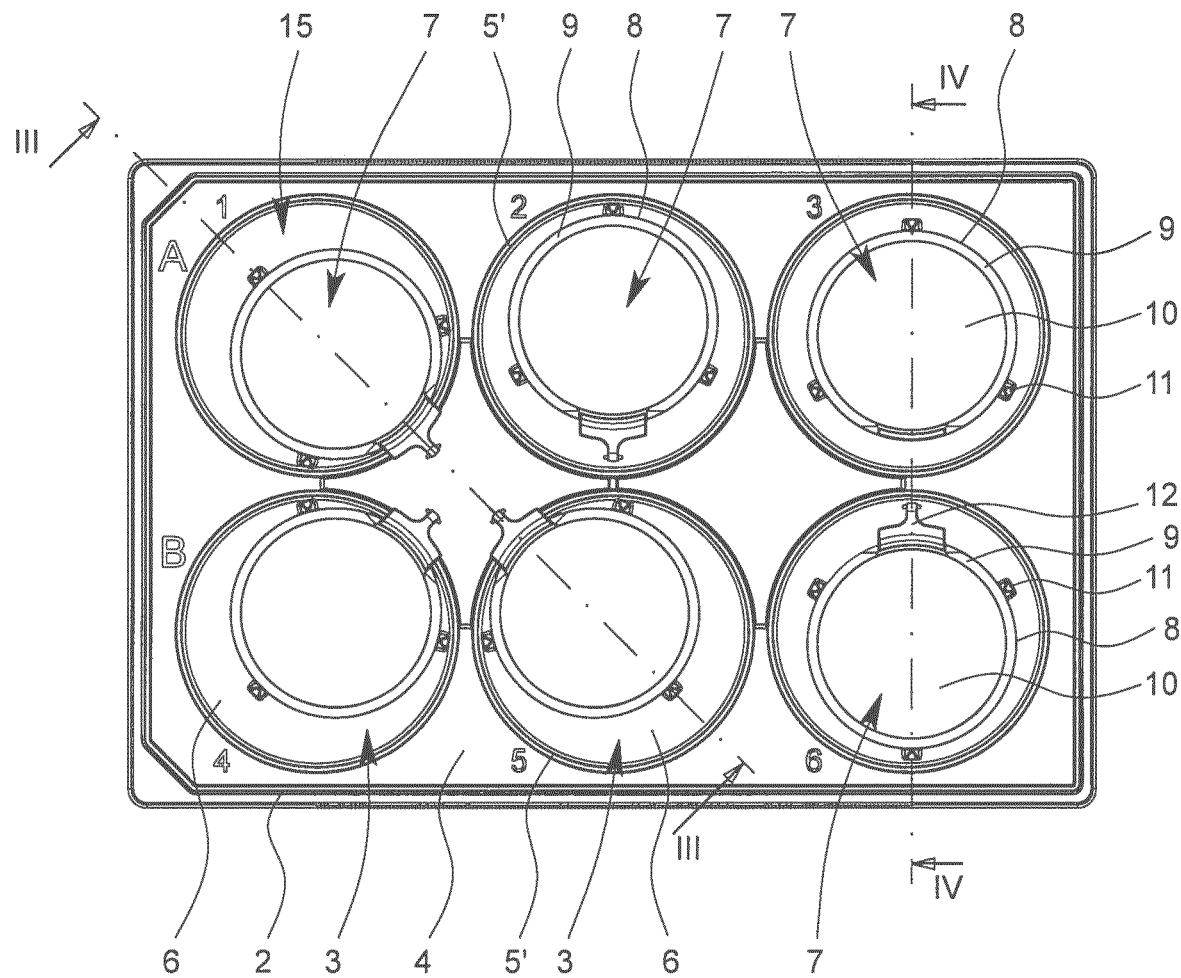
FIG. 2 is a top view of the device shown in FIG. 1.
Figure 3:
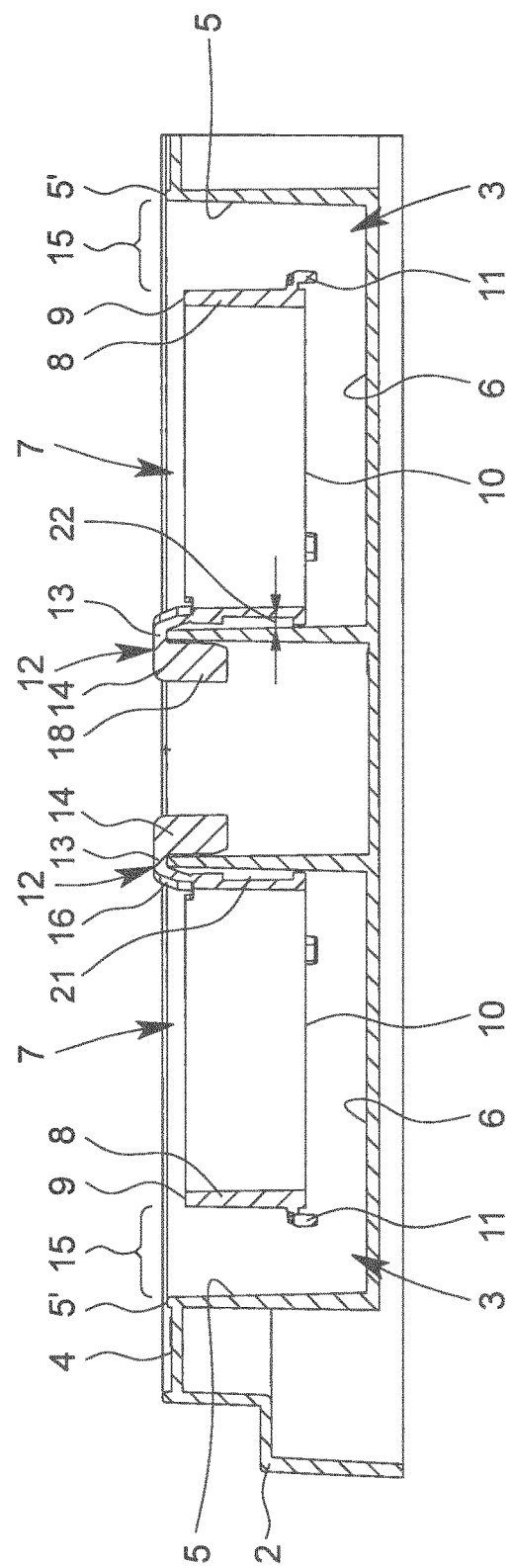
FIG. 3 is a sectional view of the device taken line in FIG. 2.
Figure 4:
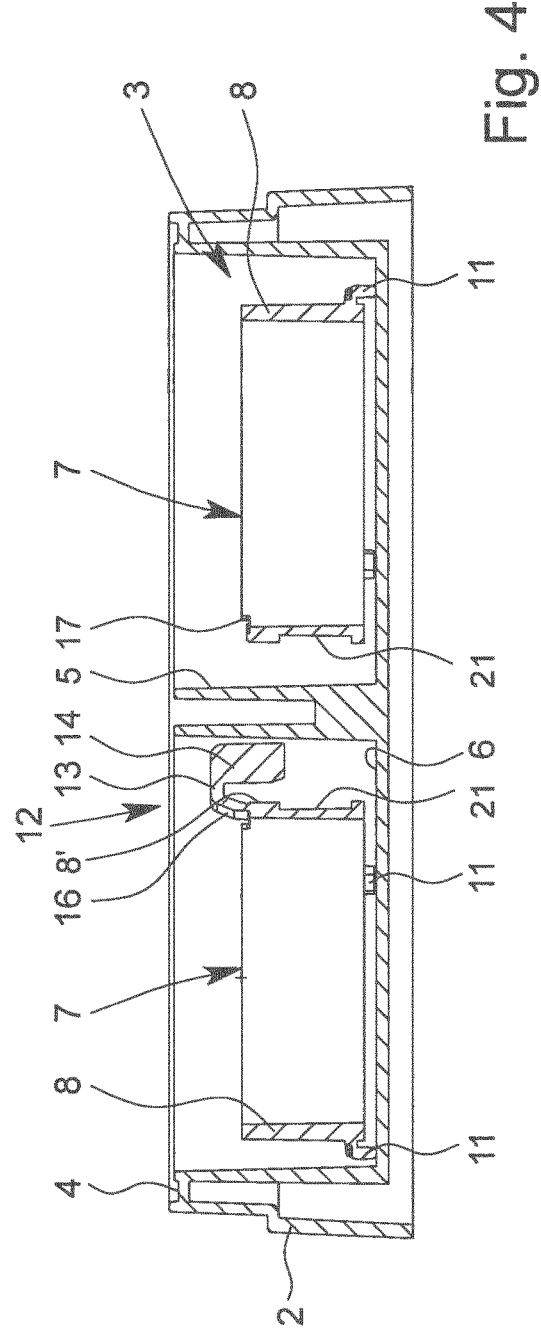
FIG. 4 is a sectional view of the device taken line IV-IV in FIG. 2.
Figure 5:
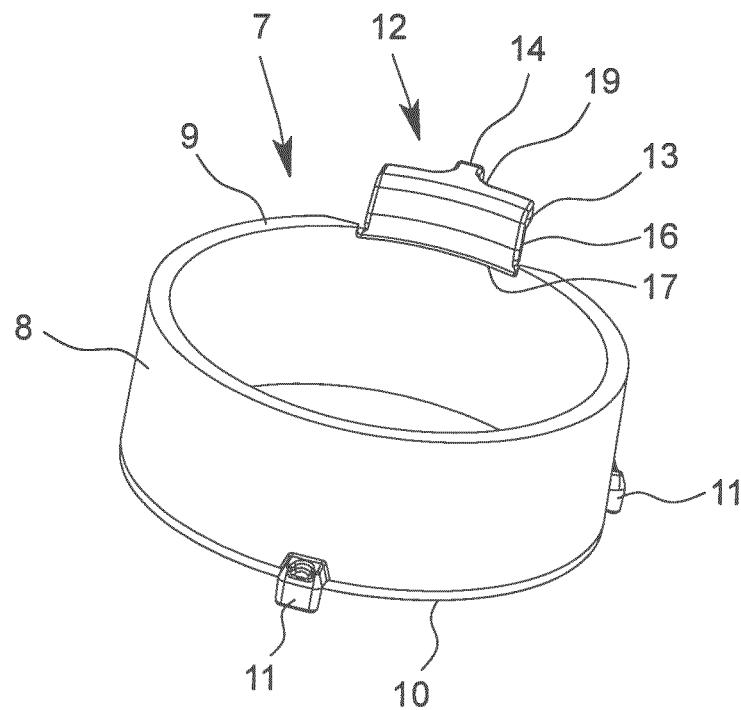
FIG. 5 is a perspective view seen obliquely from above a cell culture insert according to the invention.
Figure 6:
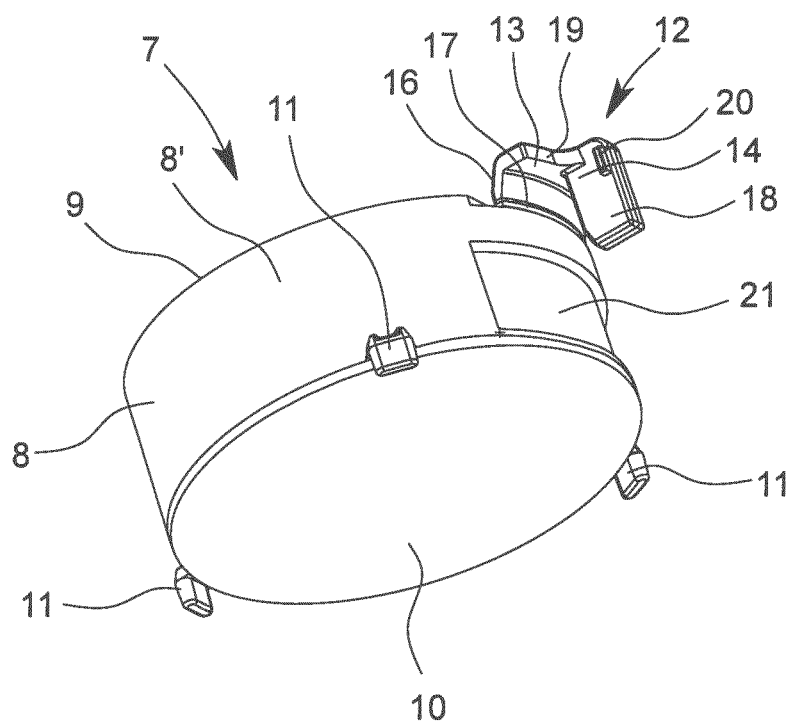
FIG. 6 is a perspective view seen obliquely from beneath the cell culture insert of FIG. 5.

FIG. 1 shows a cell culture insert 7 in the wells 3 associated with the identifying numbers 1, 2, 4, and 5 on the top side 4 of the well plate 2. FIG. 2 shows cell culture inserts not only in the four wells 3 mentioned above, but there are also cell culture inserts 7 in the wells at the far right having the identifying numbers 3 and 6. FIGS. 3 and 4 show the sections of the apparatus illustrated in FIG. 2. FIGS. 5 and 6 show a preferred cell culture insert 7 according to the invention in two different perspective views.

Reference is made below to all figures in association.

The cell culture insert 7 according to the invention has a hollow cylindrical housing 8 with an upper opening at the end, bordered by an edge 9, and a lower bottom 10, embodied as a membrane, on the end face, with supporting feet 11, arranged at the bottom edge of the housing 8 and/or on the bottom 10 and protruding downward. With these supporting feet, the housing 8 can be placed in a tilt-proof manner on a substrate at a slight but uniform distance of the bottom 10 from the substrate. The housing also has at least one carrying arm 12, which protrudes outward from the housing 8 on the edge 9 of the opening, and can be placed on an edge 5' of a well 3 of a well plate 2.

In the embodiment illustrated here, the supporting feet 11 on the bottom-side edge of the housing 8, but not on the bottom 10, can be seen well in the sectional views of FIGS. 3 & 4. In other embodiments, however, the supporting feet 11 may also be arranged directly on the bottom 10 or in the transition between the housing 8 and the bottom 10.

Furthermore, FIG. 3 also shows particularly well that the bottom 10 is embodied as a thin permeable membrane. This corresponds to the typical construction of cell culture inserts 7. Suitable suggestions from the state of the art cited in the introduction can be applied here, in particular with regard to the choice of materials for the bottom 10 and the manner, in which the bottom 10 is installed on the housing 8 of the cell culture insert 7.

It can be seen from FIGS. 3, 4 and FIG. 6, in particular, that the cell culture insert 7 according to the invention has a carrying arm 12 embodied as an edge suspension element, and for this purpose, has a supporting section 13 running radially relative to the housing 8 and a suspension section 14 running downward from the supporting section 13 in a direction toward the bottom 10 of the housing 8. In a circular cylindrical housing 8, "radial" is an unambiguous specification, in a non-circular cylindrical housing 8, this refers to the orientation from the edge of the housing 8 outward.

It can be seen in FIG. 3 how the cell culture insert 7 according to the invention can easily be suspended loosely in the well 3 with the carrying arm 12. It can be seen well here that the edge 9 of the opening of the cell culture insert 7 in the well 3 is beneath the edge 5' of the well 3. With the suspended cell culture insert 7, the supporting feet 11 are arranged at a distance from the bottom 6 of the well 3. The outside height of the cell culture insert is thus less than the inside height of the well 3.

It can be seen from FIGS. 2, 3 and 4 that in the embodiment shown here, the cell culture insert 7 has certain lateral outside dimensions, and the lateral outside dimensions of the cell culture insert 7, and that the lateral outside dimensions of the cell culture insert 7 are smaller than the lateral inside dimensions of the well 3, not taking into account the at least one carrying arm 12, namely such that the housing 8 of the cell culture insert 7 on the side opposite the suspended carrying arm 12 has a much greater distance from the side wall 5 of the well 3 than on the side of the housing 8 facing the carrying arm 12. FIG. 3 shows that there is a large feed-through window 15 in the well 3 opposite the respective carrying arm 12, so that culture medium can be added to the well 3 or removed from the well 3 by means of a pipette tip. Accordingly, the feed-through window 15 can also be seen well in FIGS. 1 and 2.

FIG. 4 shows that, in comparing the cell culture insert 7 at the left in the well 3 and the one at the right in the neighboring well 3, the lateral outside dimensions of the cell culture insert 7 are smaller than the lateral inside dimensions of the well 3, taking into account the at least one carrying arm 12, and that the cell culture insert 7 together with the at least one carrying arm 12 can therefore be deposited on the bottom 6 of the well 3. The location of the section can be seen in FIG. 2. One can see a greater distance from the side wall 5 of the well 3 than on the side of the housing 8 facing away from the carrying arm 12 at the lower right of FIG. 2 in a well 3 with the number 6 at the upper right and also at the left next to the suspension section 14 of the carrying arm 12 there. The distance at the right and left of the carrying arm 12 creates a sufficiently large feed-through window 15.

FIG. 3 shows that with the suspended cell culture insert 7, the clearance distance of the suspension section 14 of the housing 8 is greater than the thickness of the edge 5' of a well 3, thereby resulting in a clearance fit for the inserted cell culture insert 7 in the well 3. This is readily understandable on the basis of the gap illustrated there.

The preferred embodiment of a cell culture insert 7 shown in FIGS. 5 and 6 also illustrates a special structural feature, i.e., that the carrying arm 12 has an initial section 16 running upward from the housing 8 and followed by the supporting section 13, namely in such a way that, with the cell culture insert suspended in the well 3, the edge 9 of the opening lies beneath the edge 5' of the well 3. As a result, the position of the edge 9 of the opening of the cell culture insert 7 is slightly below the edge 5' of the side wall 5 of the well 3, as can be seen well at the right and left of the drawing in FIG. 3. The vertical position of the cell culture insert 7 in the well 3 of the well plate 2 is predetermined by the design of the carrying arm 12 in the various sections.

On the carrying arm 12 at the upper right, FIG. 6 shows, as another special feature of the cell culture insert 7 according to the invention, that the carrying arm 12 has a predetermined breaking point 17 here and preferably in the initial section 16 near the housing 8, wherein the carrying arm 12 can be broken off the housing 8 there, and the predetermined breaking point 17 is preferably embodied in the form of an arc of a circle, so that it has good flexural stability. A predetermined breaking point 17 has already been recommended in the state of the art for carrying arms 12 of the type in question. It runs here in the form of an arc of a circle on the housing 8, because the housing 8 of the cell culture insert 7 is designed here as a circular cylinder on the whole.

FIG. 4 shows at the right here a cell culture insert 7 without the carrying arm 12, which has already been broken off. It can be seen that a great deal of space is available here at the right and left of the cell culture insert 7.

FIGS. 1 and 6 together illustrate another particular feature of the cell culture insert 7 according to the invention, which relates to the manageability of the cell culture insert 7 by means of tweezers. Namely, with this construction, it is provided that the suspension section 14 of the carrying arm 12 extended outward is designed as a grip bar 18 for a gripping tool, in particular tweezers. The tweezers (not shown here) can act on the surfaces of the grip bar 18 at the right and left. However, they do not slip down from the grip bar 18, because curved recesses 19 at the right and left and also elevated moldings 20 on both sides of the grip bar 18 in this example surround and thus hold and guide the legs of the tweezers in a form-fitting manner With this design, the cell culture insert 7 can thus be transported in a stable position by means of tweezers or some other gripping tool.

The cell culture insert 7 shown on an enlarged scale in two perspective views illustrated in FIGS. 5 and 6 has a most expedient design in particular, namely having exactly one carrying arm 12 on the housing 8 instead of having a plurality of carrying arms 12. This single carrying arm serves to suspend the cell culture insert 7 on the edge 5' of the well 3. This is sufficient; no more carrying arms are needed for the cell culture insert 7 according to the invention. This is a simple design and saves on material. Due to the suspension section 14, the carrying arm 12 according to the invention fulfills the function implemented in the state of the art by means of a plurality of carrying arms 12 on the housing 8 of the state-of-the-art cell culture insert 7.

The figures also show a special feature of the design according to the invention, which is characterized in that the supporting feet 11 also protrude outward from the housing 8, with two supporting feet 11 on the circumference of the housing 8 are arranged at the same distance from the carrying arm 12 on each side. In this way, when the suspended cell culture insert 7, the supporting feet 11 cooperate with the carrying arm 12 to the extent that, on the whole, this yields a three-point bearing of the housing 8 of the cell culture insert 7 on the side wall 5 of the well 3 (carrying arm 12, first supporting foot 11, second supporting foot 11). This can be understood readily on the basis of FIGS. 6 and 3.

With a correct arrangement of the various components, one can achieve the result that the arrangement of the suspension section 14 of the carrying arm 12, on the one hand, and the supporting feet 11 associated with the carrying arm 12, on the other hand, is selected so that a cell culture insert 7 suspended in the well 3 is arranged at an inclination of no more than 10° with respect to the well 3. This can be seen in the diagram in FIG. 3, where the angle of inclination is approximately 3°.

Here and preferably on the outside circumference 8' of the housing 8, the cell culture insert 7 illustrated in FIG. 6 has an indentation 21 vis-à-vis the carrying arm 12. This indentation 21 extends symmetrically with the carrying arm 12 on the outside circumference 8' and along the housing 8. The indentation 21 is formed adjacent the bottom 10 and amounts to at least 50% of the outside height of the cell culture insert 7. The position and height of the indentation 21 are adapted to the level of liquid in the well 3. The level is always higher than the height of the bottom 10 of a cell culture insert 7 deposited on the supporting feet 11 or hanging in the well 3.

As shown in FIG. 3, the distance between the side wall 5 and the outside circumference 8' of the suspended cell culture insert 7 is minor or almost zero. The indentation 21 interrupts a capillarity of fluid in the well 3, which occurs in the critical area between the side wall 5 and the outside circumference 8'. The indentation 21 has corresponding dimensions on the outside circumference 8' and ensures that the fluid added does not rise much higher in this critical area than its level in the well 3. The level influenced by the capillarity should remain at least within the height of the indentation 21.

The indentation 21 may be based on the outside circumference 8' and may be similar or of a different depth, as shown in FIG. 6. The depth in this embodiment is selected so that the distance 22 between the indentation 21 of the suspended cell culture insert 7 and the side wall 5 in the critical area is not less than 1 mm. The capillarity is influenced by the distance 22, the liquid density, the surface tension of the liquid at the outside circumference 8' and/or of the indentation 21 and the side wall 5.

In the illustrated and preferred embodiment, it is provided throughout that the housing 8 of the cell culture insert 7 is embodied as a circular cylinder. This is expedient in particular but not obligatory. Other lateral cross sections of cell culture inserts 7 are also disclosed in the state of the art as well as the corresponding cross sections of wells of corresponding well plates. According to the invention, however, it is particularly expedient if both the wells 3 of the well plate 2 and the housing 8 of the cell culture inserts 7 are embodied as circular cylinders.

For the cell culture inserts 7 as well as for the well plate 2, it is true that plastic, in particular a thermoplastic polymer, is preferably used. Examples of this were given in the introduction, but there are also numerous examples in the state of the art.

All of the aspects of the invention described above can be used individually as well as in combination with one another.

What is claimed is:

1. A device for culturing cells comprising:
   a well plate in which a plurality of wells is formed to hold liquid, wherein each well has a bottom and has a peripheral side wall protruding therefrom, wherein the side wall has a top edge terminating the side wall, and wherein each well has certain lateral inside dimensions in a plane parallel to the bottom, and wherein each well has a certain inside height in a direction perpendicular to the bottom, and
   a cell culture insert having an outside height, wherein the cell culture insert has a carrying arm for suspending of the culture insert on the top edge of the well and supporting feet,
   wherein the cell culture insert has a housing and lateral outside dimensions, and the lateral outside dimensions of the cell culture insert are smaller than the lateral inside dimensions of the well, not taking into account the carrying arm, such that the housing of the cell culture insert suspended with the carrying arm on the top edge of the well has a greater distance from the side wall of the well on a side opposite the carrying arm than on the side of the housing at which the carrying arm is located.

2. The device according to claim 1, wherein the lateral outside dimensions of the cell culture insert are smaller than the lateral inside dimensions of the well, taking into account the carrying arm so that the cell culture insert together with the carrying arm can be deposited on the bottom of the well.

3. The device according to claim 1, wherein the lateral geometric shape of the well is asymmetrical relative to the lateral geometric shape of a housing of the cell culture insert.

4. The device according to claim 3, wherein the well plate is made of a thermoplastic polymer.

\* \* \* \* \*